(12) United States Patent
Howard et al.

(10) Patent No.: US 10,111,752 B2
(45) Date of Patent: Oct. 30, 2018

(54) CRANIOPLASTY PLATE

(71) Applicant: University of Iowa Research Foundation, Iowa City, IA (US)

(72) Inventors: Matthew A. Howard, Iowa City, IA (US); Nicole M. Grosland, Iowa City, IA (US); Kingsley Adobe-Iyamah, Iowa City, IA (US); Kirsten E. Stoner, Iowa City, IA (US); Oliver Flouty, Iowa City, IA (US); C. Allan Guymon, Iowa City, IA (US); Brian James Green, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 15/080,647

(22) Filed: Mar. 25, 2016

(65) Prior Publication Data
US 2017/0273794 A1    Sep. 28, 2017

Related U.S. Application Data

(60) Provisional application No. 62/138,769, filed on Mar. 26, 2015, provisional application No. 62/166,746, filed on May 27, 2015.

(51) Int. Cl.
*A61F 2/02* (2006.01)
*A61F 2/28* (2006.01)
*A61F 2/30* (2006.01)

(52) U.S. Cl.
CPC ........ *A61F 2/2875* (2013.01); *A61F 2/30724* (2013.01); *A61F 2/30749* (2013.01); *A61F 2002/30062* (2013.01); *A61F 2002/30115* (2013.01)

(58) Field of Classification Search
CPC .......................... A61F 2/2875; A61B 17/8028
See application file for complete search history.

(56) References Cited

U.S. PATENT DOCUMENTS

| 5,628,748 | A  | 5/1997  | Vicari          |
|-----------|----|---------|-----------------|
| 6,350,284 | B1 | 2/2002  | Tormala et al.  |
| 2007/0191848 | A1 | 8/2007 | Wack et al.    |
| 2008/0208347 | A1 | 8/2008 | Muratoglu et al. |
| 2010/0256641 | A1 | 10/2010 | Rabiner et al. |

OTHER PUBLICATIONS

University of Iowa Research Foundation, PCT/US2016/024244 filed Mar. 25, 2016, "The International Search Report adn the Written Opinion of the International Searching Authority, or the Declaration", dated Jun. 17, 2016, 10 pages.

*Primary Examiner* — Brian Dukert
(74) *Attorney, Agent, or Firm* — Thomas C. Saitta (57) ABSTRACT

A cranial plate is provided for use after a craniectomy. The plate is mounted to the skull and protects the brain exposed in the skull opening. A plate is initially spaced above the skull with gaskets or spacers so as to preclude pressure on the brain. The gaskets or spacers are resorptive, or otherwise dissolve or shrink over time, until the plate settles upon the skull. An elastic web extending over the plate provides a constant force to pull the plate towards the skull as the spacers shrink. The plate is secured to the skull using screws. The plate may include alignment posts residing adjacent the skull opening to maintain proper positioning of the plate as the spacers shrink. The plate eliminates the need for a second cranioplasty surgical procedure.

19 Claims, 8 Drawing Sheets

CRANIOPLASTY PLATE

CROSS-REFERENCE TO RELATED APPLICATION(S)

This is a conversion of and claims a benefit of priority from U.S. Provisional Application No. 62/138,769, filed Mar. 26, 2015, entitled "CRANIOPLASTY PLATE," as well as U.S. Provisional Application No. 62/166,746, filed May 27, 2015 entitled "CRANIOPLASTY PLATE WITH ELASTIC FASTENERS," which are hereby incorporated by reference as if set forth herein in their entireties.

BACKGROUND OF THE INVENTION

A craniectomy is a medical surgical procedure commonly performed to manage intractable brain swelling, often caused by trauma or stroke. When a patient is managed using a standard craniectomy procedure, two surgeries are required. First, a craniotomy is performed, wherein a section of the skull is removed and then the skin or scalp is closed over the skull opening. The craniectomy allows for the brain tissue to expand through the opening to reduce intracranial pressure. After the brain swelling has receded, which may take several weeks or months, a second cranioplasty operation is required to replace the saved native bone material, or alternatively, to implant a prosthetic skull piece, such as a thin titanium skull plate. This second operation restores a solid covering over the skull opening or defect.

The removal of the skull section in the craniectomy allows the brain tissue to expand without restriction by the skull. Without the skull protection, the brain is vulnerable under the skin until swelling reduces in the following weeks or months, until the cranioplasty surgery takes place to repair the skull defect. During the interim between the craniectomy and the cranioplasty procedures, the patient normally wears a helmet to protect the brain. The cranioplasty surgery increases the high costs associated with patient care. The cranioplasty procedure also increases the patient risk, with potential brain damage from the significant manipulation of the brain which can cause intracranial hemorrhage and seizures, increased risk of infection, and wound breakdown. Also, prior to the cranioplasty, patients often develop headaches and have delays in their recovery due to the loss of normal intracranial pressure gradient provided by the skull.

Therefore, a primary objective of the present invention is the provision of a craniectomy surgical procedure which achieves both the decompression and relief of intracranial pressure and a protective solid covering over the skull opening, with only one surgical operation.

Another objective of the present invention is a provision of an improved cranial plate for use after a craniectomy.

A further objective of the present invention is a provision of a cranial plate having a gasket or spacer to position the plate above the skull.

A further objective of the present invention is the provision of a cranial plate having elastic, or moveable elements that exert a force to maintain the position of the plate relative to the skull and pulls the plate towards the skull as spacers resorb.

Still another objective of the present invention is a provision of an improved cranial plate with a spacer between the plate and the skull, with a spacer shrinking over time so that the plate settles onto the skull.

Yet another objective of the present invention is a provision of a cranial plate which can be implanted during a craniectomy operation, without the need for a follow up cranioplasty operation.

Another objective of the present invention is a provision of a surgical procedure wherein a portion of the skull is removed to expose the brain, and a plate is positioned over the skull, in the appropriate spatial relationship to the skull defect, and then over time settles onto the skull, without a second surgical procedure.

Still another objective of the present invention is a provision of a craniectomy surgical procedure wherein resorptive spacers or mechanical elements that contracted over time, are used between a patient's skull and a cranial plate.

A further objective of the present invention is a provision of the improved cranial plate which is economical to manufacture, simple to implant, and safe for the patient.

These and other objectives have become apparent from the following description.

SUMMARY OF THE INVENTION

A craniectomy plate is formed as a mesh titanium body to cover the skull opening and the brain. The plurality of spaces on the perimeter edge of the plate positions the plate at a spaced distance above the skull. Over time, the spaces shrink, such as by resorption of spacers or contraction of mechanical fastening elements so that the plate settles onto the skull.

The craniotomy surgical procedure removes a section of the skull, and replaces the removed section with a plate spaced from the skull on spacers or contractible mechanical elements which shrink or contract over time, until the plate settles on the skull, thereby eliminating the need for cranioplasty surgery.

DETAILED DESCRIPTION OF THE INVENTION

FIGS. 1-3 show the preliminary steps of a craniotomy surgical procedure.

FIGS. 4-10 show a first embodiment of the cranioplasty plate of the present invention.

FIG. 11-13 show a second embodiment of the cranioplasty plate of the present invention.

FIG. 14-18 show a third embodiment of the cranioplasty plate of the present invention.

DETAILED DESCRIPTION OF THE INVENTION

The present invention is directed towards a cranial plate and a method of surgically installing the cranial plate during a craniectomy neurosurgical procedure.

Figure 5:
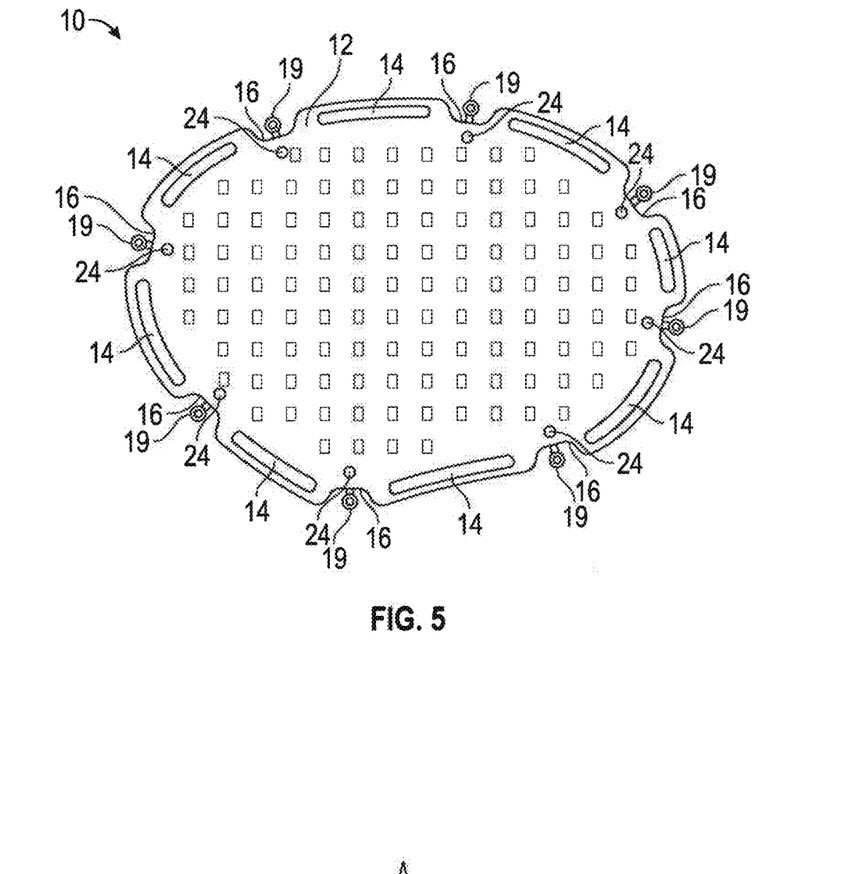
FIG. 5 is a bottom plan view of the interior surface of the cranial plate of the present invention.
Figure 6:
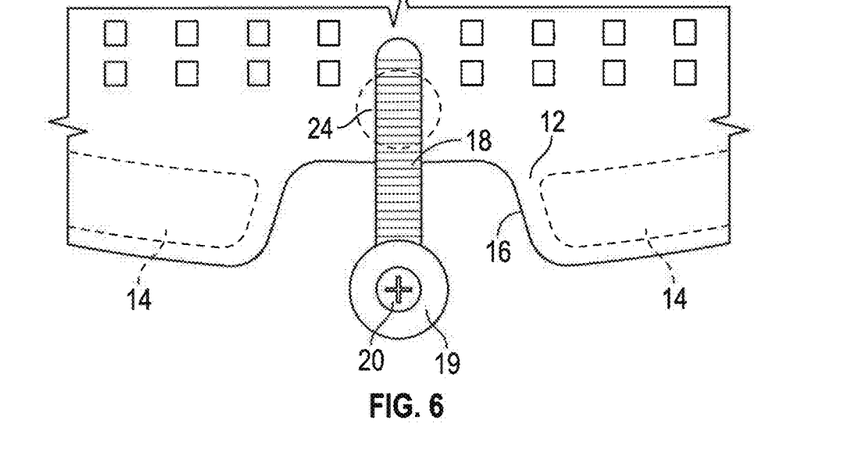
FIG. 6 is an enlarged top plan view of a portion of the plate showing one of the fasteners for the plate of FIG. 4.
Figure 7:
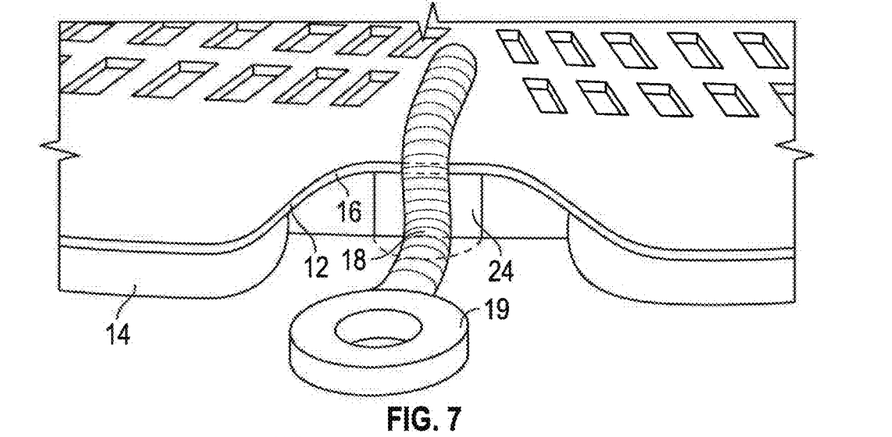
FIG. 7 is an upper perspective view of the cranial plate of FIG. 4 and one of the fixture mechanisms according to the present invention, without the screw for clarity.

In a first embodiment of the invention shown in FIGS. 4-9, the cranioplasty plate 10 includes a mesh body 12, with a re-absorbable polymeric gasket or gaskets 14 along the periphery of the body. Preferably, the body 12 is made from a strong, rigid, yet light weight material, such as titanium. As seen in FIGS. 5-7, the body 12 may include a series of spaced apart perimeter notches or indentations 16, with the resorbable gaskets 14 positioned between the notches 16. Alternatively, a gasket 14 can extend continuously 360 degrees along the perimeter of the body 12.

The plate 10 also includes a plurality of malleable, non-absorbable fasteners, such as elastic elements, 18 with end eyelets 19, fixed to the body 12 and extending radially outwardly. Each eyelet 19 is adapted to receive a cranial screw 20 to fix the plate 10 to a patient's skull 22. The plate 10 also includes a series of stabilizing posts 24 which extend downwardly from the bottom of the plate 10 adjacent the edge of the skull opening 23 to ensure proper positioning of the plate 10. Preferably, the gaskets 14 are made of a resorbable polymeric material which gradually breaks down over time. Alternatively, the gaskets can be formed with inflatable and deflatable balloons, a dissolving hydrogel material, or other water-deswelling material.

Figure 11:
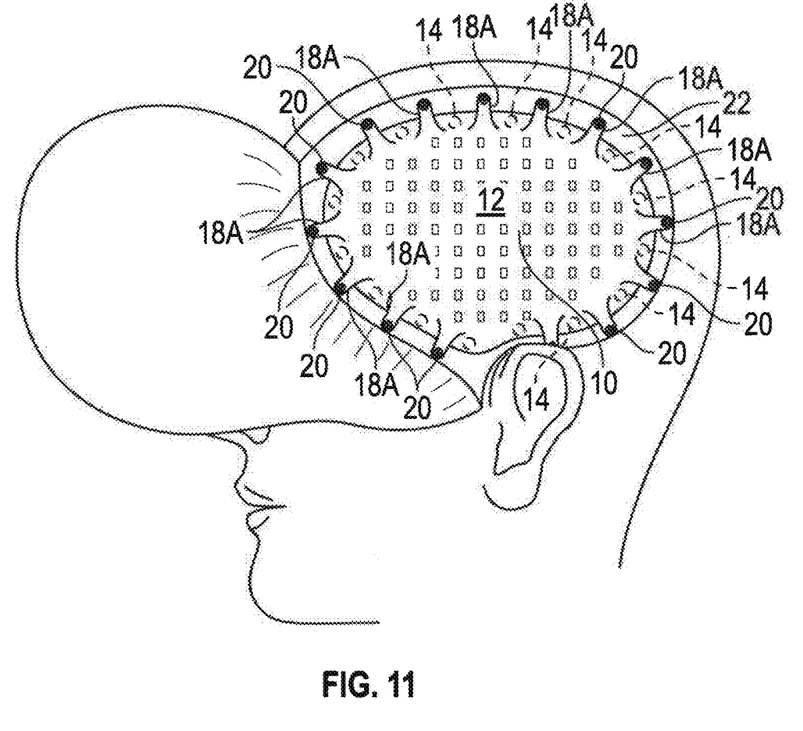
FIG. 11 is a side elevation view of a person's head showing a second embodiment of the cranial plate of the present invention positioned over the skull opening and secured with cranial screws.
Figure 12:
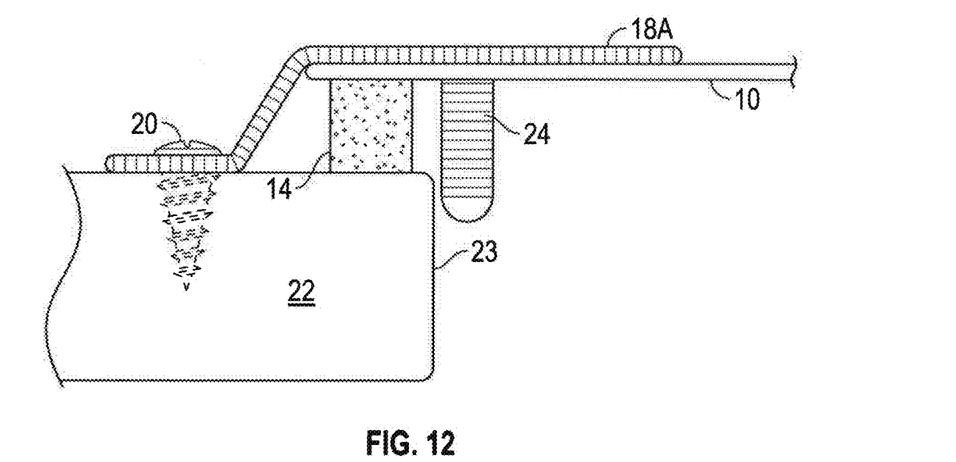
FIG. 12 is a side elevation view of the second embodiment of the cranial plate attached to the skull and spaced above the skull by one of a plurality of spacers, in accordance with the present invention.
Figure 13:
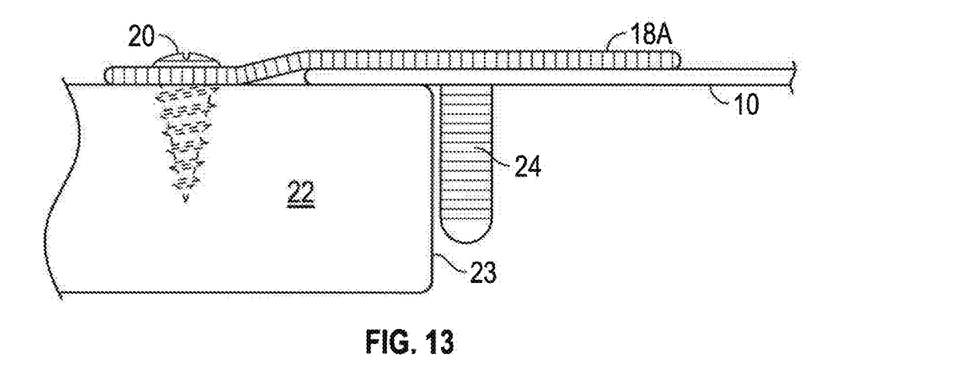
FIG. 13 is a side elevation view showing the second embodiment of the cranial plate engaging the skull after the spacers have been resorbed over time.
Figure 14:
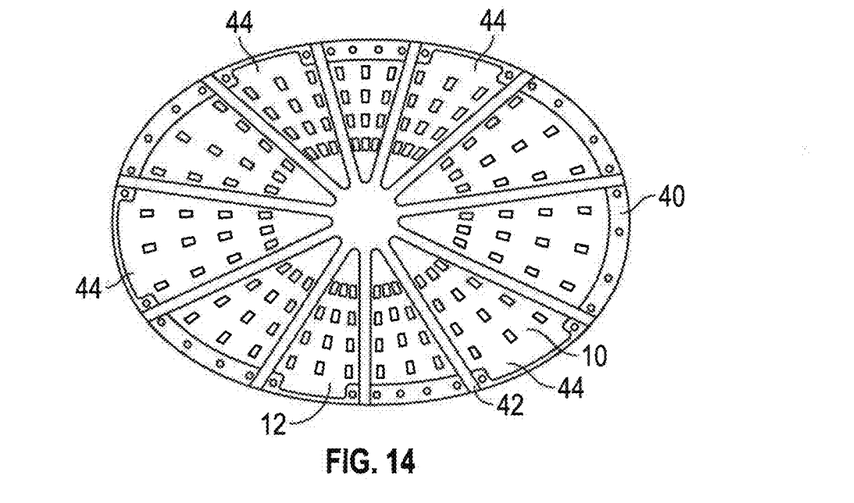
FIG. 14 is a top plan view of another embodiment of a mesh cranial plate with an elastic web positioned over the plate so as to pull the plate downwardly.
Figure 15:
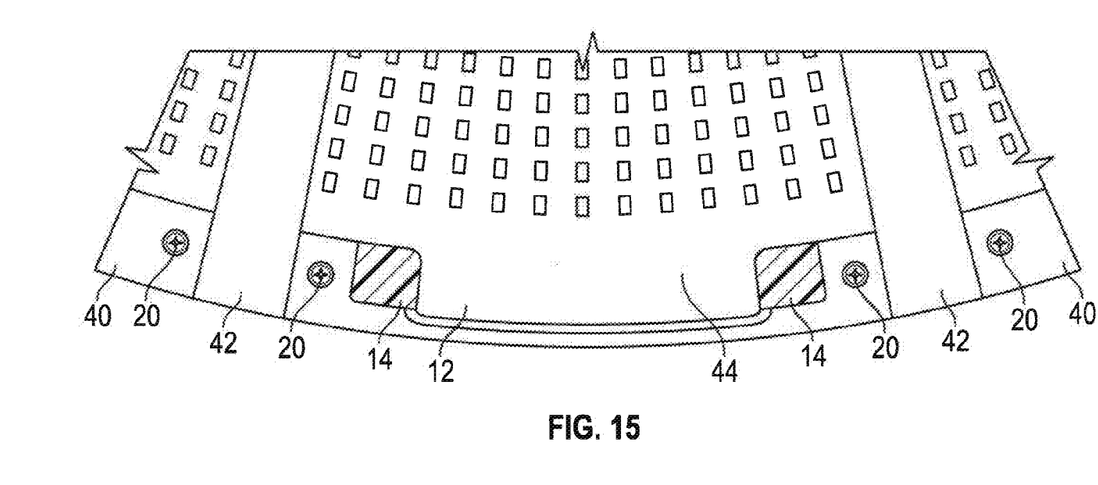
FIG. 15 is an enlarged top plan view of a portion of the plate and web shown in FIG. 14.
Figure 16:
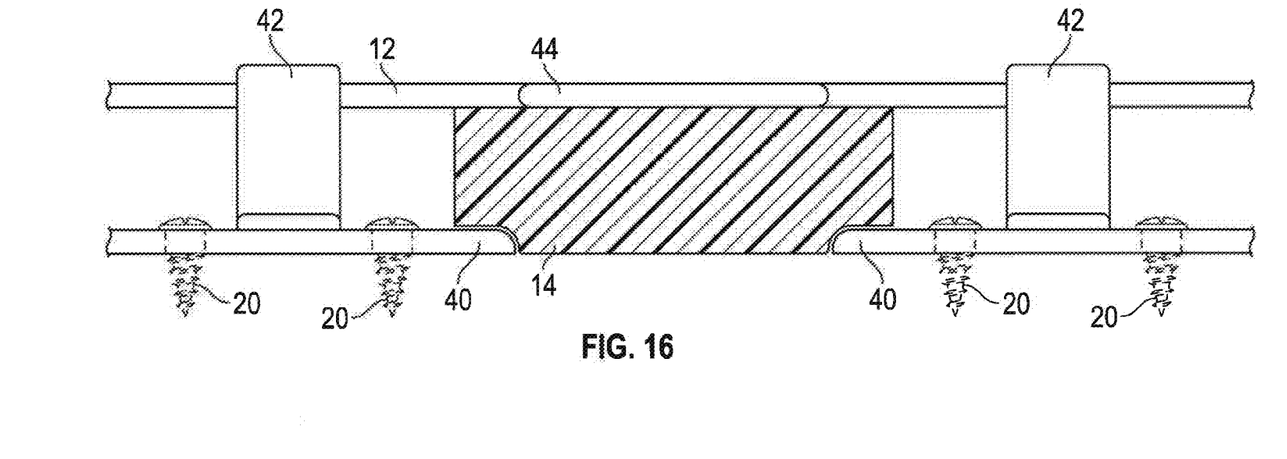
FIG. 16 is a side elevation view of the plate and web shown in FIG. 14.
Figure 17:
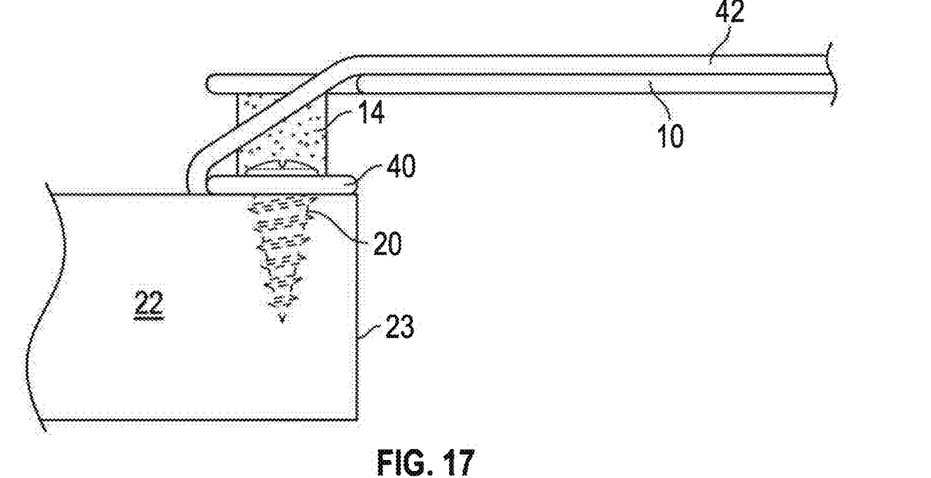
FIG. 17 is an enlarged side elevation view of the plate and web of FIG. 14, as initially installed during the craniotomy surgical procedure, with the plate spaced above the skull.
Figure 18:
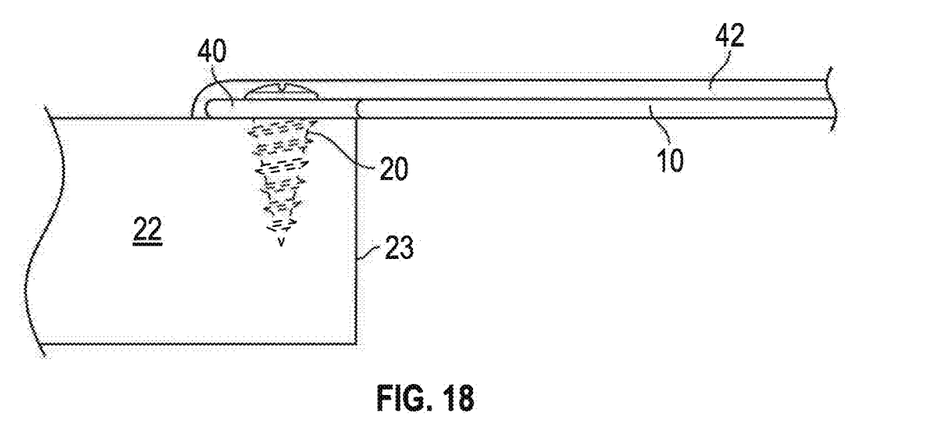
FIG. 18 is a view similar to 17, wherein the spacer has dissolved and the plate has settled on the skull.

In an embodiment shown in FIGS. 11-13, the cranioplasty plate 10 includes a titanium mesh body 12 with a plurality of spaced apart re-absorbable polymeric spacers 14, such as Vicryl® cylinders, along the periphery of the body 12. Preferably, the spacers 14 are made of a re-absorbable polymeric material which gradually breaks down over time.

The plate 10 includes a plurality of elastic fasteners or bands 18 fixed to the body 12 and extending radially outwardly. The inner ends of the fasteners 28 are attached to the plate 10 in any convenient manner, such as by an adhesive. Elastic fastener 18 has an outer end adapted to receive a cranial screw 20 to fix the plate 10 to a patient's skull 22. The outer ends of the fasteners 18 may be formed with an eyelet (not shown) through which the screw 20 extends. Alternatively, the screws 20 can be pushed through the fastener material.

Figure 8:
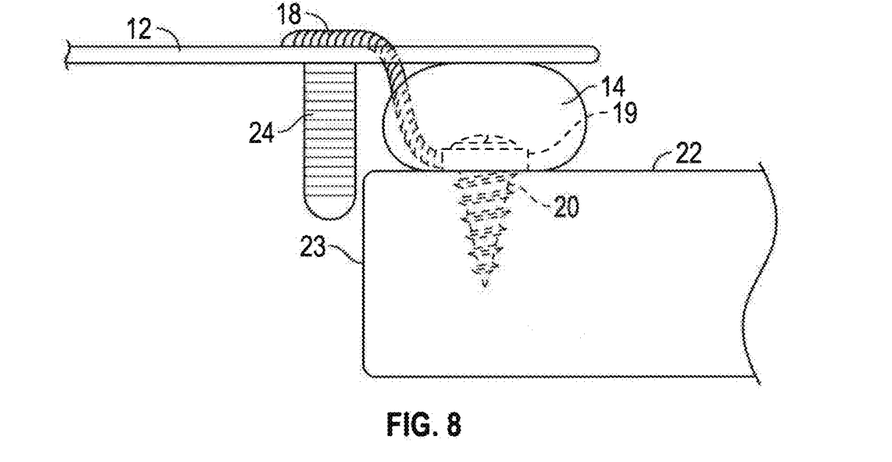
FIG. 8 is a side elevation view of the cranial plate attached to the skull and spaced above the skull by the gasket, according to the first embodiment of the present invention.
Figure 9:
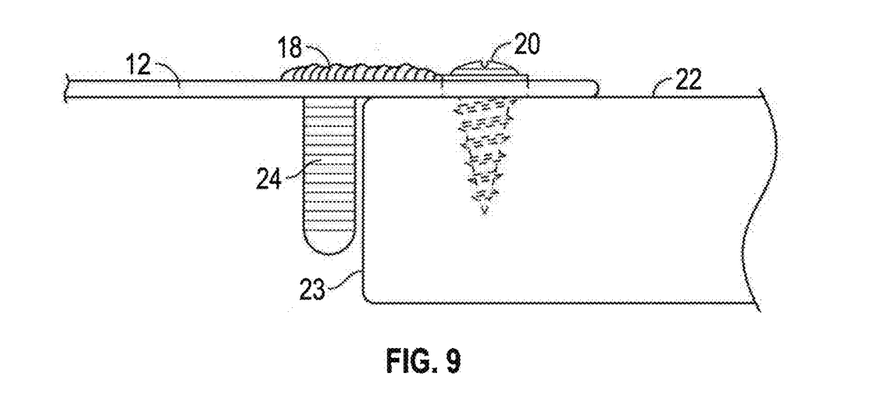
FIG. 9 is a side elevation view showing the cranial plate engaging the skull after the gasket has been resorbed over time, according to the first embodiment of the invention.
Figure 10:
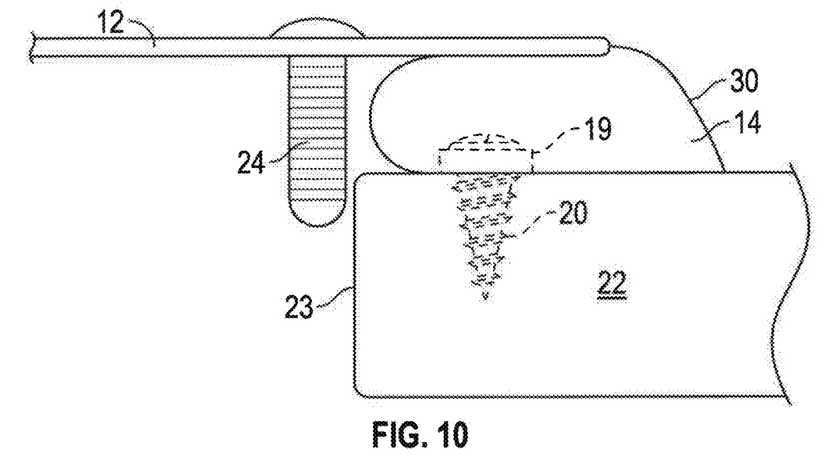
FIG. 10 is a side elevation view similar to FIG. 7 showing an alternative embodiment of the gasket.

The gaskets or spacers 14 function to space the body 12 above or away from the skull 22, thereby allowing intracranial pressure relief. The spacing is approximately 5 millimeters between the plate 10 and the skull 22. This initial spacing is maintained for approximately 2 weeks, and then decreases over time as the spacers 18 shrink. As brain swelling recedes over time, the gasket material or spacers are absorbed by the skin, or the gaskets or spacers 14 are otherwise deflated or dissolved so that eventually the body 12 is substantially flush with the skull 22. The gaskets 14 ensure the elevated position of the plate 10 and spatial separation from the skull 22 during the period of brain swelling, as seen in FIGS. 7 and 9. The eyelets 19, screws 20, and stabilizing posts 24 assures proper alignment of the plate 10 over the skull opening 23 throughout the evolving stages of post-implementation time period. The position of the posts 24 inside the skull opening 23 allows the plate body 12 to drop onto the skull 22 as the gaskets 14 shrink over time. As the gasket 14 shrinks, the stabilizing posts 24 ensure that the body 12 of the plate 10 settles optimally over the skull defect 23, as shown in FIG. 8. The elastic fasteners 18 pull the plate 10 towards the skull 22 as the spacers 14 shrink.

In an alternative embodiment, the gaskets 14 may extend beyond the perimeter of the body 12 with a tapered edge 30, as shown in FIG. 9, to prevent or minimize scalp wound healing problems, and provide a smooth transition between the edge of the body 12 and the underlying skull 22. In a further alternative, the gasket(s) can be attached or secured to the native bone.

As another alternative, the plate 10 may include a locking mechanism to further secure the plate 10 to the skull 22 after resorption or deflation of the gaskets 14. For example, the locking mechanism may consist of a male end on the underside of the body 12 and a female end on the body adjacent the edge of the skull opening. The male and female ends can be pushed together after the body 12 has receded onto the skull 22 so as to lock the plate and skull together. Another example is a zip-lock type mechanism with percutaneous screws.

In a further alternative, the fasteners may be any element that pulls the plate towards the skull as the spacer or gasket retracts. For example, the pulling force can be achieved with metal springs, contracting metal spacers, or a linear actuation, such as a miniature electric motor with a remote controller.

Thus, the cranioplasty plate and procedure of the present invention reduces healthcare costs and associated risks, as compared to the conventional two-step craniectomy and cranioplasty procedures.

Another embodiment of the present invention is shown in FIGS. 14-18. In this embodiment, the plate 10 is attached at its perimeter to a cranial interface fixation ring 40. An elastic web 42 extends over the mesh body 12 and the ring 40 of the plate 10. The screws 20 extend through the ring 40 and into the skull to secure the plate 10 in position. The elastic web 42 asserts a relatively constant force across the body 12 so as to pull the body toward the ring 40. The body 12 includes perimeter tabs 44 which overlie the spacers 14. The ring 40 may also include downwardly extending posts, similar to posts 24 on the other embodiments described previously, to help maintain alignment of the ring 40 and the body 12 as the spacers 14 shrink or dissolve. The elastic web 42 is preferably made from material that is biocompatible and FDA approved, such as a polydimethylsiloxane (PDMS). The ring 40 eliminates the need for the surgeon to place the elastic fasteners on a stretch when placing the bone screws. Thus, the ring 40 is pre-loaded.

Figure 1:
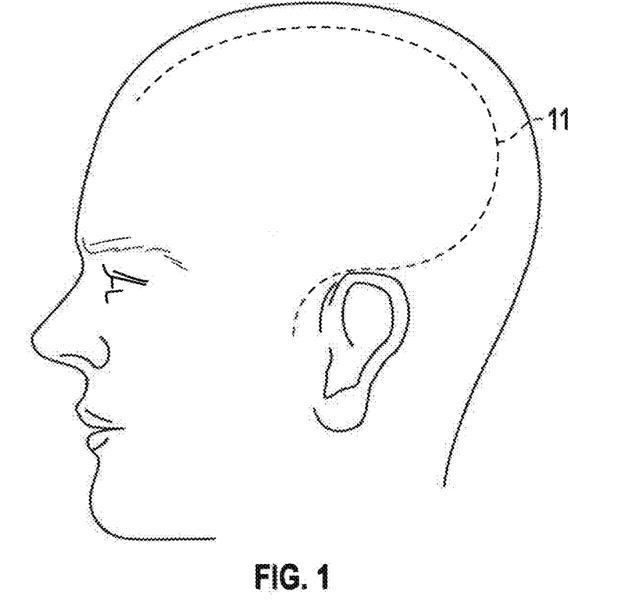
FIG. 1 is a side elevation view showing a person's head with a standard question mark shaped trauma flap of a craniotomy.
Figure 2:
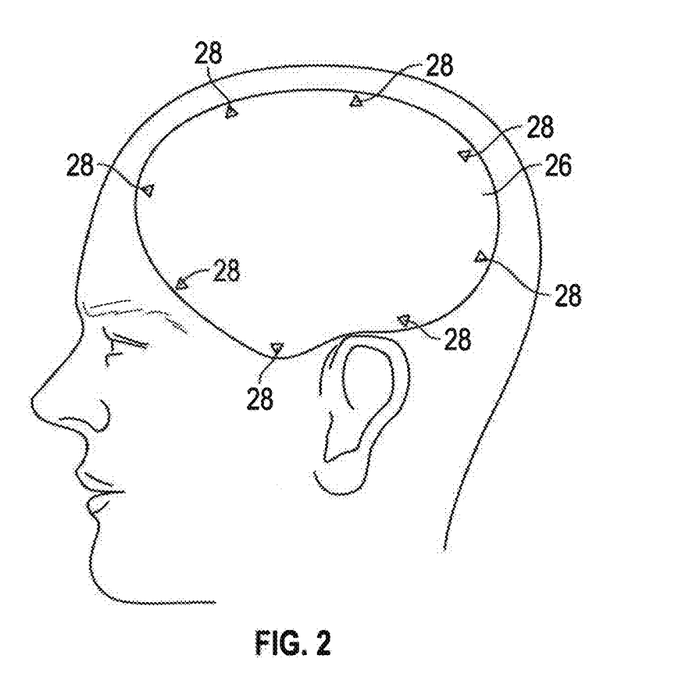
FIG. 2 is a side elevation view of a person's head showing the placement of a template for the cranial plate according to the present invention.
Figure 3:
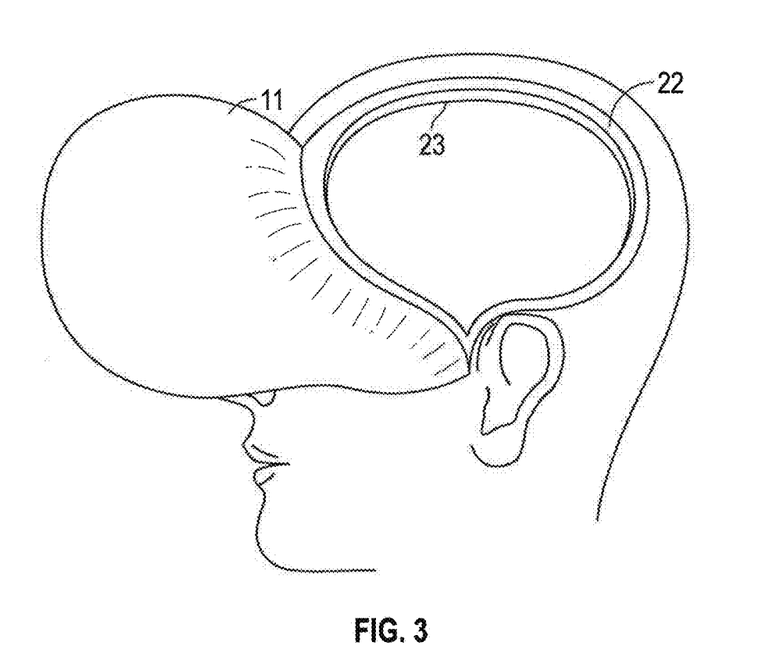
FIG. 3 is a side elevation view showing an opening in the skull after a portion of the skull is removed.
Figure 4:
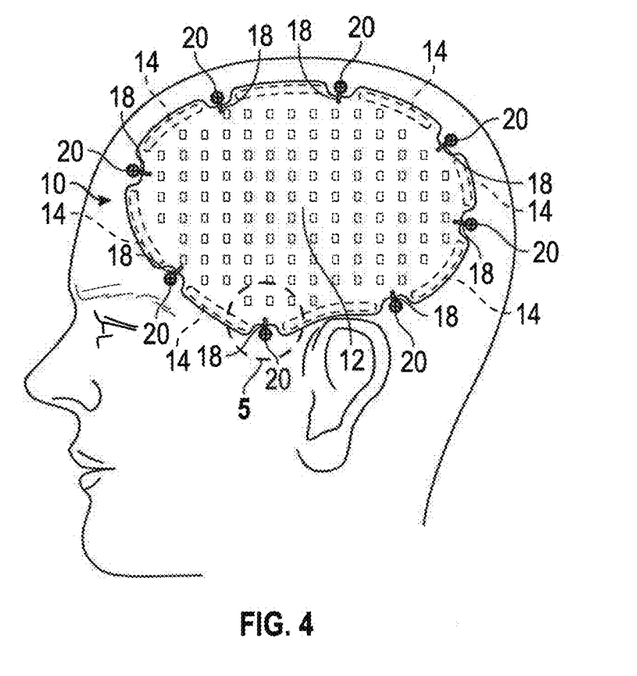
FIG. 4 is a side elevation view of a person's head showing a first embodiment of the cranial plate of the present invention positioned over the skull opening and secured with cranial screws.

The neurosurgical method of the present invention involves first step of exposing the skull using a standard trauma flap 11 cut in the skin, as shown in FIG. 1. A template 26 is positioned over the skull opening 23 so that the surgeon or medical personnel can mark the boundary of the template 26 and the locations 28 for the fixture screws, as shown in FIG. 2. The template border defines the subsequent bone cut or cuts to be made by the surgeon. The template 26 is then be removed.

Next, the surgeon performs the craniotomy, cutting the skill bone along the marked lines of the template to remove a portion of the skull, such that the skull opening 23 matches the template size and shape. Once the dura is opened, the brain is decompressed in standard fashion. Artificial dura may be placed over the exposed brain.

Then, the surgeon positions the cranioplasty plate 10 with the full gaskets or spacers 14 over the skull opening 23, such that the fixation points defined by the eyelets 19 or the webs 42 are aligned with the fixation location marks 28. The surgeon then installs standard cranial screws 20 through the eyelets 19 or web material 42 to secure the cranioplasty plate 10 at the fixation points 28. The circumferential arrangement of the fasteners 20 around the perimeter edge of the plate 10 prevents displacement of the plate. The gaskets or spacers 14 adjacent the edge of the skull opening 23 ensure proper initial positioning of the plate 10 above the skull 22. With the second and third embodiments, the fasteners 18 are stretched when initially secured to the skull 22, so as to apply a downward force on the plate 10 towards the skull. Thus, the elastic fasteners 18A pull the plate toward the skull 22. The surgical procedure closes with the installation of a subgaleal drain (not shown) and closing of the skin flap 11 using staples or stitches.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A cranioplasty plate, comprising: a body adapted to cover a skull opening exposing the brain and having opposite upper and lower surfaces and a perimeter edge; a gasket on the lower surface of the body adjacent the perimeter to space the body apart from the skull; the gasket being adapted to shrink over time so that the body settles onto the skull;
   elastic fasteners fixed to the body and extending radially outward; and
   cranial screws adapted to fix the elastic fasteners to the skull;
   whereby the elastic fasteners pull the body towards the skull as the gasket shrinks over time.

2. The cranioplasty plate of claim 1 wherein the gasket is made of resorbable material.

3. The cranioplasty plate of claim 1 wherein the gasket is an inflatable and deflatable balloon.

4. The cranioplasty plate of claim 1 wherein the gasket is a hydrogel material.

5. A cranioplasty plate, comprising: a body adapted to cover a skull opening exposing the brain, the plate having opposite upper and lower surfaces and a perimeter edge; a plurality of spacers on the lower surface of the body adjacent the perimeter to space the body above the skull; the spacers being adapted to shrink over time so that the body settles onto the skull;
   elastic fasteners fixed to the body and extending radially outward; and
   cranial screws adapted to fix the elastic fasteners to the skull;
   whereby said elastic fasteners pull the body towards the skull as the spacers shrinks over time.

6. The cranioplasty plate of claim 5 wherein the spacers are made of resorbable material.

7. The cranioplasty plate of claim 5 wherein each elastic fastener has an inner end fixed to the body and an outer end adapted to be secured to the skull.

8. The cranioplasty plate of claim 1, each of the elastic fasteners comprising an eyelet adapted to receive one of the cranial screws.

9. The cranioplasty plate of claim 1, wherein the elastic fasteners are fixed to the body by an adhesive.

10. The cranioplasty plate of claim 1, wherein the cranial fasteners are pushed through the elastic fasteners.

11. The cranioplasty plate of claim 1, the skull opening having an edge, the cranioplasty plate further comprising stabilizing posts extending from the lower surface of the body toward the skull opening, said stabilizing posts disposed adjacent the edge of the skull opening to ensure proper positioning of the plate as the gasket shrinks over time.

12. The cranioplasty plate of claim 1, wherein the elastic fasteners are disposed in a stretched status between the cranial fasteners and the body prior to the gasket shrinking.

13. The cranioplasty plate of claim 1, wherein the elastic fasteners are characterized as spontaneously returning to normal shape when a tensile farce is removed.

14. The cranioplasty plate of claim 7, wherein the outer end of each of the elastic fasteners comprises an eyelet adapted to receive one of the cranial screws.

15. The cranioplasty plate of claim 5, wherein the elastic fasteners are fixed to the body by an adhesive.

16. The cranioplasty plate of claim 5, wherein the cranial fasteners are pushed through the elastic fasteners.

17. The cranioplasty plate of claim 5, the skull opening having an edge, the cranioplasty plate further comprising stabilizing posts extending from the lower surface of the body toward the skull opening, said stabilizing posts disposed adjacent the edge of the skull opening to ensure proper positioning of the plate as the spacers shrink over time.

18. The cranioplasty plate of claim 5, wherein the elastic fasteners are disposed in a stretched status between the cranial fasteners and the body prior to the spacers shrinking.

19. The cranioplasty plate of claim 5, wherein the elastic fasteners are characterized as spontaneously returning to normal shape when a tensile force is removed.

* * * * *